United States Patent
Receveur

(10) Patent No.: US 7,853,328 B2
(45) Date of Patent: *Dec. 14, 2010

(54) CHIP LEVEL BIOSTABLE INTERCONNECT FOR IMPLANTABLE MEDICAL DEVICES

(75) Inventor: Rogier Receveur, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 306 days.

This patent is subject to a terminal disclaimer.

(21) Appl. No.: 11/735,832

(22) Filed: Apr. 16, 2007

(65) Prior Publication Data

US 2007/0260287 A1    Nov. 8, 2007

Related U.S. Application Data

(63) Continuation-in-part of application No. 11/114,451, filed on Apr. 26, 2005, now Pat. No. 7,228,177.

(51) Int. Cl.
*A61N 1/375* (2006.01)

(52) U.S. Cl. .......................................... 607/37

(58) Field of Classification Search ............... 607/37, 607/36, 38

See application file for complete search history.

(56) References Cited

U.S. PATENT DOCUMENTS

| | | | | |
|---|---|---|---|---|
| 5,045,151 | A | * | 9/1991 | Edell ........................... 257/622 |
| 5,564,434 | A | | 10/1996 | Halperin et al. |
| 5,877,472 | A | | 3/1999 | Campbell et al. |
| 5,961,849 | A | * | 10/1999 | Bostock et al. ............... 216/24 |
| 5,973,906 | A | | 10/1999 | Stevenson et al. |
| 6,433,411 | B1 | | 8/2002 | Degani et al. |
| 6,452,238 | B1 | | 9/2002 | Orcutt et al. |
| 6,638,784 | B2 | | 10/2003 | Bartlett et al. |
| 6,743,656 | B2 | | 6/2004 | Orcutt et al. |
| 6,969,639 | B2 | | 11/2005 | Cho et al. |
| 7,065,867 | B2 | | 6/2006 | Kim et al. |
| 2004/0040735 | A1 | | 3/2004 | Ciurzynski et al. |

FOREIGN PATENT DOCUMENTS

EP    0 380 237 A1    8/1990

OTHER PUBLICATIONS

European Examination Report for European Patent Application No. 06 740 930.0-2305, Jul. 1, 2009; 3 pgs.
International Search Report for PCT Application No. PCT/US2006/013868, Sep. 27, 2006; 3 pgs.
Written Opinion of the International Searching Authority for PCT Application No. PCT/US2006/013868, Oct. 26, 2007; 6 pgs.

* cited by examiner

*Primary Examiner*—Carl H Layno
*Assistant Examiner*—Brian T Gedeon
(74) *Attorney, Agent, or Firm*—Carol F. Barry

(57) ABSTRACT

A lead is connected to an integrated circuit in an implantable medical device in a lead bonding area that includes a lead-receiving recessed region. At least a portion of a lead conductor is bonded in the lead-receiving recessed region, making an electrical and mechanical connection to the integrated circuit that is strong and potentially biostable. In some embodiments, a filler material is provided around the recessed portion of the integrated circuit that receives the lead conductor, and a metal coating is provided around an outer surface of the filler material for additional mechanical stability.

21 Claims, 3 Drawing Sheets

CHIP LEVEL BIOSTABLE INTERCONNECT FOR IMPLANTABLE MEDICAL DEVICES

RELATED APPLICATIONS

This application is a continuation-in-part of application Ser. No. 11/114,451, filed Apr. 26, 2005 now U.S. Pat. No. 7,228,177, entitled "Chip Level Biostable Interconnect for Implantable Medical Devices."

BACKGROUND OF THE INVENTION

The present invention relates to a biostable interconnect for an implantable medical device.

Implantable medical devices (IMDs) employ internal electronic circuitry (typically implemented as integrated circuits (ICs)), sensors and other components that are hermetically sealed in a biostable package. The IMD package is designed to be biostable to prevent failure due to attacks from the defense system of the body in which the IMD is implanted. One particular aspect of the package that is designed to avoid failure is the conductive interconnect between a lead of the device and the internal circuitry. In addition, it is desirable for the interconnect design to be small in size to allow for relatively easy implementation in miniature IMDs.

One existing design for an IMD that is known to be biostable is a "titanium can" design, which provides a titanium structure surrounding the internal circuitry of the device. A lead of the device connects to the internal circuitry via a feedthrough pin that extends through the titanium structure and is conductively bonded to the internal circuitry. While this design has been proven to provide excellent biostability, it may be possible to achieve a biostable design that is more compact and potentially less expensive. Such a design is the subject of the present invention.

BRIEF SUMMARY OF THE INVENTION

The present invention is an interconnect design for an implantable medical device that connects a lead to an integrated circuit in a lead bonding area that includes a lead-receiving recessed region. At least a portion of a lead conductor is bonded in the lead-receiving recessed region, making an electrical and mechanical connection to the integrated circuit that is strong and potentially biostable. In some embodiments, a filler material is provided around the recessed portion of the integrated circuit that receives the lead conductor, and a metal coating is provided around an outer surface of the filler material for additional mechanical stability.

DETAILED DESCRIPTION

Figure 1:
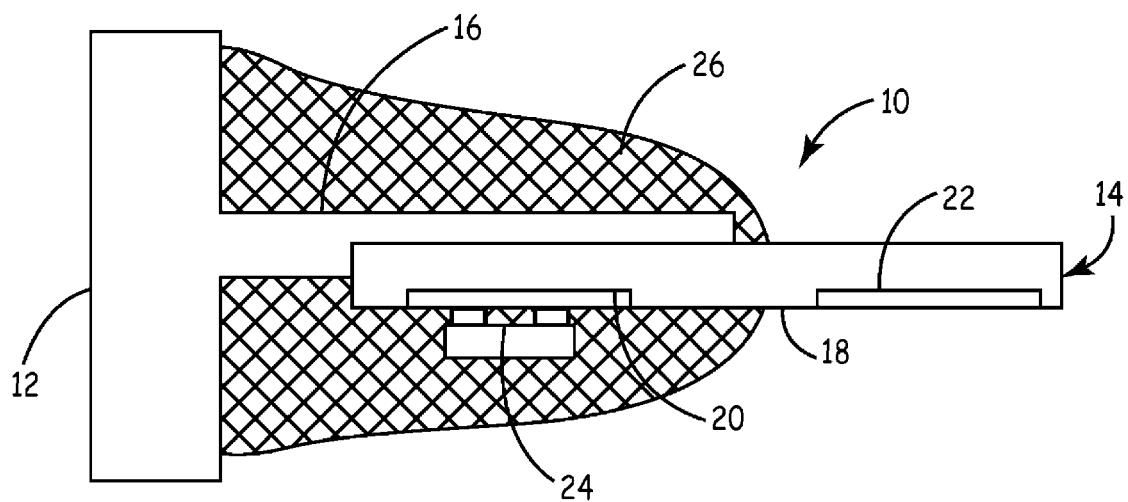
FIG. 1 is a diagram illustrating an interconnect between a lead and an integrated circuit in an implantable medical device according to an embodiment of the present invention.

FIG. 1 is a diagram illustrating interconnect 10 between lead 12 and integrated circuit 14 according to an embodiment of the present invention. Lead 12 includes lead conductor 16 extending away from a main body of lead 12. Lead conductor 16 is bonded to integrated circuit 14, which is a structure that includes substrate or body 18 carrying electronics 20 and pressure sensor 22. Integrated circuit 14 also carries capacitor 24, which is mounted on the portion of substrate 18 that carries electronics 20. Non-conductive filler material 26, such as silicone in one embodiment, is provided around interconnect 10 where lead conductor 16 is bonded to integrated circuit 14, for mechanical stability and to electrically insulate lead conductor 16. Pressure sensor 22 projects beyond filler material 26, so that the operation of pressure sensor 22 is not affected by material on its outer surface.

Although lead conductor 16 has been described and shown as extending away from a main body of lead 12, it should be understood by those skilled in the art that a number of other arrangements of lead 12 could be employed in the configuration of interconnect shown in FIG. 1. For example, lead 12 may be arranged, as is known in the art, with a lead body forming a filled sleeve around lead conductor 16. In this arrangement, filler material 26 is realized by the lead body (rather than by separately deposited material) around lead conductor 16. The lead body in this arrangement could even extend completely over the portion of integrated circuit 14 that carries pressure sensor 22, leaving an internal cavity open for operation of pressure sensor 22. In this particular configuration, the distal part of the lead body is made of a relatively stiff material. Other arrangements will be apparent to those skilled in the art.

Figure 2:
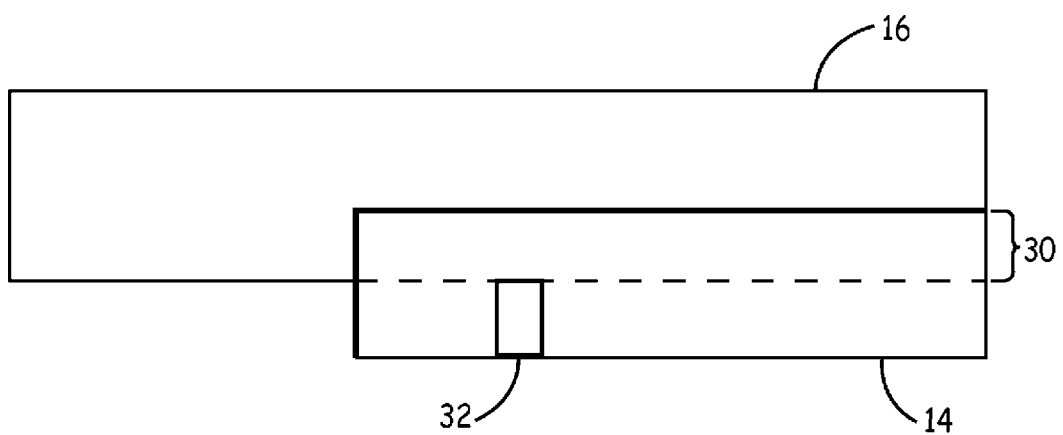
FIG. 2 is a side view of an interconnect between a lead conductor and an integrated circuit according to an embodiment of the present invention.
Figure 3A:
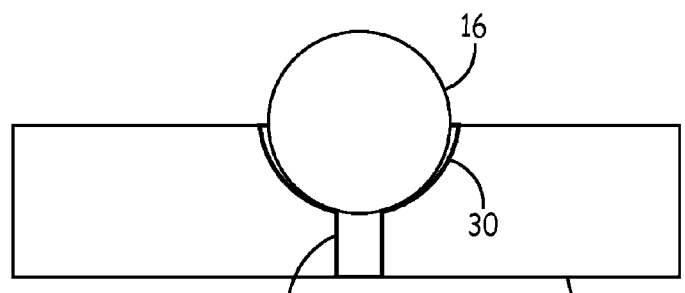
FIGS. 3A, 3B and 3C are end views of various embodiments of the interconnect between a lead conductor and an integrated circuit as shown in FIG. 2.
Figure 3B:
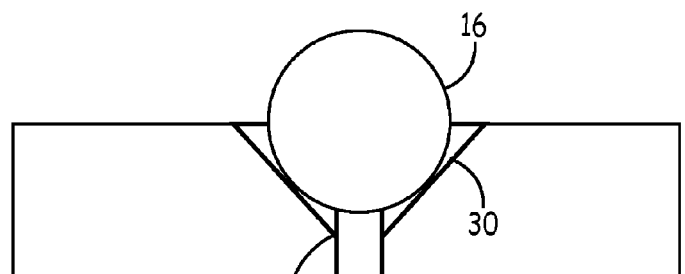
Figure 3C:
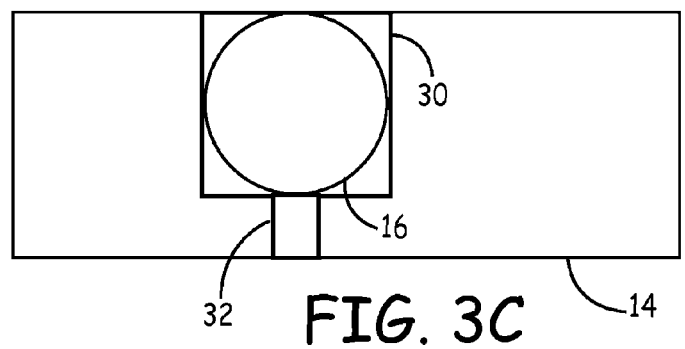

FIG. 2 is a side view, and FIGS. 3A, 3B and 3C are end views of various embodiments of interconnect 10 between lead conductor 16 and integrated circuit 14. As shown in FIG. 2, lead conductor 16 is bonded to integrated circuit 14 in recessed region 30, and conductive via 32 extends through integrated circuit 14 to contact electronics 20 (FIG. 1) that are carried on the bottom of integrated circuit 14. FIG. 3A shows an embodiment where recessed region 30 is semicircular in shape, FIG. 3B shows an embodiment where recessed region 30 is triangular in shape, and FIG. 3C shows an embodiment where recessed region 30 is square in shape. The embodiment shown in FIG. 3C receives all of lead conductor 16 into recessed region 30, although in other embodiments recessed region 30 may be formed with less depth, so that a portion of lead conductor 16 protrudes from the upper surface of integrated circuit 14.

All of the shapes of recessed region 30 shown in FIGS. 3A, 3B and 3C (semicircle, triangle, and square/rectangle, respectively), as well as combinations of these shapes, are readily achievable by microfabrication processing techniques known in the art. For example, the semicircular shape of recessed region 30 shown in FIG. 3A can be formed by wet isotropic etching, and the aperture for conductive via 32 can be formed to connect to recessed region 30 by sandblasting, etching, particle bombardment, or other methods. The triangular shape shown in FIG. 3B and the square/rectangle shape shown in FIG. 3C can be formed by wet etching or reactive ion etching techniques that are known in the art. Metallization of the walls of recessed region 30 can be achieved by plating, evaporation, or other known techniques, using a metal material such as niobium, platinum, tantalum, titanium, stainless steel, or others. Conductive filament can then be placed within recessed region 30, to achieve electrical connection between lead conductor 16, the metallized walls of recessed region 30, and conductive via 32. This connection is achieved by laser heating, resistance welding, or another bonding technique if needed to provide sufficient mechanical strength to interconnect 10. In one embodiment, lead conductor 16 is larger than recessed region 30, and the connection is achieved by pressing lead conductor 16 into recessed region with sufficient force to deform lead conductor 16 within recessed region 30 to achieve a mechanically secure connection.

Figure 3D:
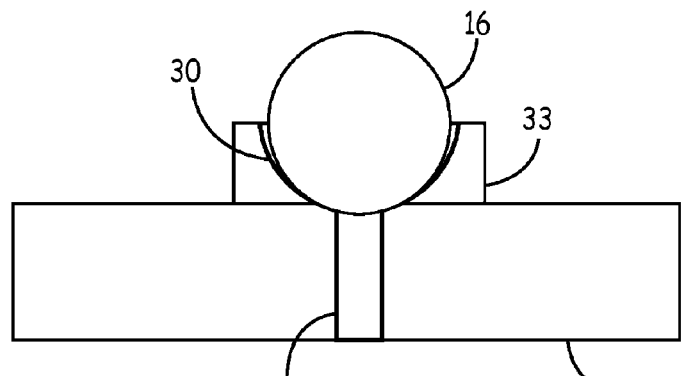
FIG. 3D is an end view of another embodiment of the interconnect between a lead conductor and an integrated circuit.

FIG. 3D is a diagram illustrating an alternative embodiment of interconnect 10 between lead conductor 16 and integrated circuit 14, in which metal lead receiving structure 33 is provided on the surface of integrated circuit 14 to receive lead conductor 16. Lead receiving structure 33 includes recessed region 30, with a shape that can be as shown in FIGS. 3A, 3B and 3C and as described above, illustrated in FIG. 3D as being a semicircular recess. Lead receiving structure 33 may be fabricated by multiple-step plating techniques, for example, or by other fabrication techniques known in the art. Lead conductor 16 is bonded in recessed region 30 of lead receiving structure 33 in the same manner described above with respect to FIGS. 3A, 3B and 3C, with electrical contact being made to conductive via 32 that extends through integrated circuit 14.

Configuring interconnect 10 to include recessed region 30 in a lead bonding area of integrated circuit 14 (either in integrated circuit 14 itself or in structure 33 formed on integrated circuit 14) that mechanically receives at least a portion of lead conductor 16 provides excellent bonding strength, and in many applications of implantable medical devices provides a bond that is biostable. The resulting configuration of integrated circuit 14, as shown in FIG. 1, is more compact than a traditional "titanium can" design due to the chip level interconnection that is employed, and also allows some functional component(s), such as pressure sensor 22 (FIG. 1), to be exposed for effective operation.

Figure 4:
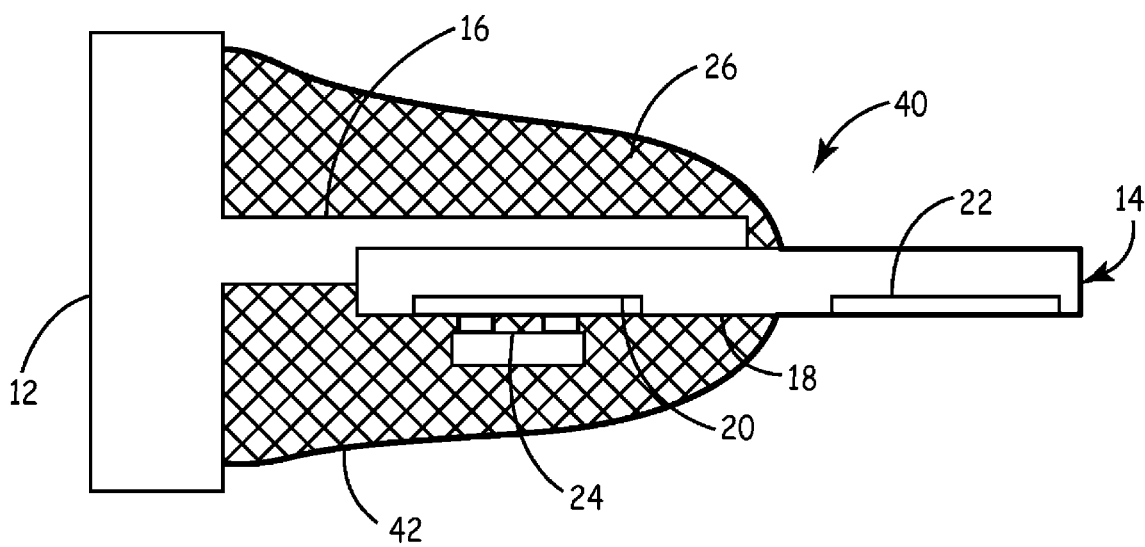
FIG. 4 is a diagram illustrating a modified version of the interconnect shown in FIG. 1.

FIG. 4 is a diagram illustrating modified interconnect 40, which is a modified version of interconnect 10 shown in FIG. 1. Interconnect 40 is identical to interconnect 10 (FIG. 1) in nearly all respects, except that interconnect 40 includes metal coating 42 (formed of titanium, another metal, or alternatively of a non-metal coating of some other sufficiently strong material) formed around the outside surfaces of filler material 26 and the exposed portion of integrated circuit 14. Metal coating 42 is provided for applications in which the interconnect design shown in FIGS. 3A, 3B, 3C and 3D is found not to be biostable. Metal coating 42 could also be provided in more traditional configurations that do not employ a recessed interconnect. Metal coating 42 provides additional mechanical integrity to interconnect 40, while being formed as a thin enough layer so as not to interfere with the operation of pressure sensor 22 in a typical embodiment. The portions of integrated circuit 14 and pressure sensor 22 that contact metal coating 42 are insulated as needed to prevent the creation of an undesirable short circuit to metal coating 42.

In one embodiment, filler material 26 is deposited as only a thin isolation coating, rather than as the relatively high volume mass of filler material shown in FIG. 4. This modification may be made to interconnect 40 because of the fact that metal coating 42 is utilized to provide mechanical integrity, which in some applications may provide biostability without the additional need for a high volume mass of filler material 26 around the interconnection between lead wire 16 and integrated circuit 14.

A further embodiment of the present invention of interconnect 50 between lead 12 and integrated circuit 14 has a configuration similar to that shown in FIG. 1, except that lead conductor 16 is received by a recessed region of integrated circuit substrate/body 18 on the same side of integrated circuit 14 on which electronics 20, pressure sensor 22 and capacitor 24 are carried. In this configuration, non-conductive filler material 26 can be provided only around the portion of interconnect 50 where lead conductor 16 is bonded to integrated circuit 14, leaving electronics 20, pressure sensor 22 and capacitor 24 uncovered by filler material 26.

In such a further embodiment, lead conductor 16 is bonded to integrated circuit 14 in recessed region 30 of integrated circuit 14. Recessed region 30 has metallization 52 on its walls, conductively contacting lead conductor 16. Metallization 52 on the walls of recessed region 30 also contacts conductive trace 54 on the surface of integrated circuit 14, which extends to electronics 20 so that a conductive path is established between lead conductor 16 and electronics 20 on integrated circuit 14.

Recessed region 30 may be semicircular in shape. In other embodiments, any of the shapes or configurations of recessed region 30 shown in FIGS. 3A, 3B, 3C and 3D could be employed to achieve the mechanical bonding strength described with respect to those figures.

The interconnect design described above with respect to embodiments of the present invention provides the ability to make a biostable connection between a lead wire and an integrated circuit of an implantable medical device at the chip level. This means that a sufficiently strong mechanical connection, able to resist the mechanical forces and chemical attacks applied by the body on the IMD, is achieved by structures that are microfabricated in the integrated circuit itself, rather than by an external bonding mechanism applied between the lead and the integrated circuit. The connection is made by forming a recessed region in a portion of the integrated circuit (or some other structure associated with or attached to the integrated circuit), and bonding the lead wire to the integrated circuit in the recessed area so that at least a portion of the lead wire is received in the recessed portion. The recessed portion is electrically connected to electronics and/or other components of the device, so that the lead wire is interconnected both electrically and mechanically. Also, as described above with respect to particular embodiments of the invention, a metal coating may be deposited around an outer surface of at least the interconnection area, to further enhance the biostability of the connection.

Although the present invention has been described with reference to preferred embodiments, workers skilled in the art will recognize that changes may be made in form and detail without departing from the spirit and scope of the invention.

The invention claimed is:

1. A lead chip level biostable interconnect structure for an implantable medical device, comprising:
    an integrated circuit having a lead bonding area that includes a lead-receiving recessed region selected from a shape of a semicircle, a triangle, a square, and a rectangle, wherein the integrated circuit carries electronics, wherein the lead-receiving recessed region comprises a region formed in a surface of the integrated circuit, wherein at least a portion of the lead-receiving recessed region is defined by one or more conductive walls; and
    a lead conductor having at least a portion thereof bonded in the lead-receiving recessed region and in contact with at least the one or more conductive walls, wherein the lead conductor is conductively connected to the electronics carried by the integrated circuit.

2. The structure of claim 1, further comprising a non-conductive filler material around the lead-receiving recessed region.

3. The structure of claim 2, wherein the integrated circuit carries a pressure sensor that is not covered by the non-conductive filler material.

4. The structure of claim 2, further comprising a metal coating over an outer surface of the filler material.

5. The structure of claim 1, wherein conductive connection between the lead conductor and the electronics carried by the integrated circuit is achieved by a conductive lining of the lead-receiving recessed region and a conductive via extending through the integrated circuit to the electronics.

6. The structure of claim 1, wherein the conductive connection between the lead conductor and the electronics carried by the integrated circuit is achieved by a conductive lining of the lead-receiving recessed region and a conductive trace on a surface of the integrated circuit extending from the lead-receiving recessed region to the electronics.

7. The structure of claim 1, wherein a capacitor is mounted to a portion of the integrated circuit that carries the electronics.

8. The structure of claim 7, further comprising a non-conductive filler material around the lead-receiving recessed region, configured so that the electronics, the capacitor and the pressure sensor carried by the integrated circuit are not covered by the non-conductive filler material.

9. The structure of claim 1, wherein the recessed region is semicircular in shape.

10. The structure of claim 1, wherein the recessed region is triangular in shape.

11. The structure of claim 1, wherein the recessed region is rectangular in shape.

12. The structure of claim 1, wherein the recessed region is square in shape.

13. The structure of claim 1, wherein all of the cross-section of at least a portion of the lead conductor orthogonal to a length of the lead conductor is received in the lead-receiving recessed region.

14. The structure of claim 1, wherein an electronic component is mounted to a portion of the integrated circuit that carries the electronics, and wherein the electronic component is covered by the non-conductive filler material.

15. The structure of claim 1, wherein the structure is locatable at a distal part of a lead body.

16. A chip level biostable interconnect for interconnecting a lead to an integrated circuit in an implantable medical device, comprising:
    a lead conductor bonded to the integrated circuit in a lead bonding area;
    a non-conductive filler material around the lead conductor in at least the lead bonding area; and
    a metal coating around an outer surface of the non-conductive filler material.

17. The interconnect of claim 16, wherein the integrated circuit carries a pressure sensor, and wherein the non-conductive filler material does not cover the pressure sensor.

18. The interconnect of claim 16, wherein the integrated circuit carries electronics conductively connected to the lead conductor by a conductive via extending through the integrated circuit in a region that is covered by the non-conductive filler material.

19. The interconnect of claim 16, wherein the integrated circuit carries electronics conductively connected to the lead conductor by a conductive trace on a surface of the integrated circuit, the electronics being located in a region that is not covered by the non-conductive filler material.

20. The interconnect of claim 16, wherein the metal coating is composed of titanium.

21. A lead chip level biostable interconnect structure for an implantable medical device, comprising:
    an integrated circuit having a lead bonding area that includes a lead-receiving recessed region selected from a shape of a semicircle, a triangle, a square, and a rectangle;
    a lead conductor having at least a portion thereof bonded in the lead-receiving recessed region; and
    a non-conductive filler material around the lead-receiving recessed region.

* * * * *